(12) United States Patent
Sasaki et al.

(10) Patent No.: US 10,849,954 B2
(45) Date of Patent: Dec. 1, 2020

(54) PREVENTIVE OR THERAPEUTIC AGENT FOR AGE-RELATED MACULAR DEGENERATION

(71) Applicant: JUNTENDO EDUCATIONAL FOUNDATION, Bunkyo-ku (JP)

(72) Inventors: Fumiyuki Sasaki, Bunkyo-ku (JP); Takehiko Yokomizo, Bunkyo-ku (JP)

(73) Assignee: JUNTENDO EDUCATIONAL FOUNDATION, Bunkyo-ku (JP)

( * ) Notice: Subject to any disclaimer, the term of this patent is extended or adjusted under 35 U.S.C. 154(b) by 0 days.

(21) Appl. No.: 15/525,660

(22) PCT Filed: Sep. 9, 2015

(86) PCT No.: PCT/JP2015/075576
§ 371 (c)(1),
(2) Date: May 10, 2017

(87) PCT Pub. No.: WO2016/076006
PCT Pub. Date: May 19, 2016

(65) Prior Publication Data
US 2017/0333516 A1  Nov. 23, 2017

(30) Foreign Application Priority Data

Nov. 11, 2014 (JP) .................... 2014-228828

(51) Int. Cl.
| | |
|---|---|
| *A61K 31/353* | (2006.01) |
| *A61K 38/05* | (2006.01) |
| *A61K 31/381* | (2006.01) |
| *A61K 31/405* | (2006.01) |
| *A61K 31/401* | (2006.01) |
| *A61K 31/4433* | (2006.01) |
| *A61K 31/192* | (2006.01) |
| *A61K 31/426* | (2006.01) |
| *A61K 31/195* | (2006.01) |
| *A61K 31/407* | (2006.01) |

(52) U.S. Cl.
CPC ............ *A61K 38/05* (2013.01); *A61K 31/192* (2013.01); *A61K 31/195* (2013.01); *A61K 31/353* (2013.01); *A61K 31/381* (2013.01); *A61K 31/401* (2013.01); *A61K 31/405* (2013.01); *A61K 31/407* (2013.01); *A61K 31/426* (2013.01); *A61K 31/4433* (2013.01)

(58) Field of Classification Search
CPC .................................................. A61K 31/353
See application file for complete search history.

(56) References Cited

U.S. PATENT DOCUMENTS 5,550,152 A * 8/1996 Koch ............... C07C 45/46
514/458

FOREIGN PATENT DOCUMENTS

WO   WO-2006011048 A1 * 2/2006 ........... A61K 31/353

OTHER PUBLICATIONS

PubChem. "Zileuton." © 2017. Available from: < https://pubchem.ncbi.nlm.nih.gov/compound/zileuton#section=Top >.*
PubChem. "Caffeic Acid." © 2017. Available from: < https://pubchem.ncbi.nlm.nih.gov/compound/caffeic_acid#section=Top >.*
Costa, M., et al. "Leukotriene B4 mediates γδ T lymphocyte migration in response to diverse stimuli." J. Leuko. Biol. (Feb. 2010), vol. 87, Issue 2, pp. 323-332.*
Sasaki, F., et al. "Leukotriene B4 receptor 1 signaling promotes neovascular age-related macular degeneration." Proceedings of the Japanese Society for Immunology. vol. 43, Nov. 2014, 3 pages (Year: 2014).*
Schwartz, S., et al. "Drug Delivery Techniques for treating age-related macular degeneration." Expert Opinion on Drug Delivery. (Nov. 13, 2013), vol. 11, Issue 1, pp. 61-68. (Year: 2013).*
International Search Report dated Oct. 20, 2015 in PCT/JP2015/075576 filed Sep. 9, 2015.
Sasaki, Fumiyuki et al., 2-C-W21-15P, "Leukotriene B4 receptor 1 signaling promotes neovascular age-related macular degeneration," Proceedings of the Japanese Society for Immunology, vol. 43, Nov. 2014, 3 pages.
Koch, Kevin et al., "(+)-1-(3S,4R)-[3-(4-Phenylbenzyl)-4-hydroxychroman-7-yl]cyclopentane Carboxylic Acid, a Highly Potent, Selective Leukotriene $B_4$ Antagonist with Oral Activity in the Murine Collagen-Induced Arthritis Model," Journal of Medicinal Chemistry, vol. 37, No. 20, Sep. 1994, pp. 3197-3199.
Evans, Jilly F. et al., "What's all the FLAP about?: 5-lipoxygenase-activating protein inhibitors for inflammatory diseases," Trends in Pharmacological Sciences, vol. 29, No. 2, 2008, pp. 72-78.
Evans, Jilly F. et al., "Bestatin inhibits covalent coupling of [$^3$H]LTA$_4$ to human leukocyte LTA$_4$ hydrolase," FEBS Letters, vol. 297, No. 1-2, Feb. 1992, pp. 139-142.
Costa, Maria Fernanda de Souza et al., "Leukotriene $B_4$ mediates gammadelta T lymphocyte migration in response to diverse stimuli," Journal of Leukocyte Biology, vol. 87, No. 2, Feb. 2010, pp. 323-332.
Sasaki, Fumiyuki et al., 3-I-W55-4-O/P, "Physiological and pathological roles of leukotriene B4 receptor 1 in M2 macrophages," Proceedings of the Japanese Society for Immunology, vol. 42, Nov. 2013, 3 pages.

(Continued)

*Primary Examiner* — John S Kenyon
(74) *Attorney, Agent, or Firm* — Oblon, McClelland, Maier & Neustadt, L.L.P.

(57) ABSTRACT

To provide a new preventive or therapeutic agent for age-related macular degeneration.
The present invention relates to a preventive or therapeutic agent for age-related macular degeneration containing a BLT1 antagonist or a LTB$_4$ biosynthesis inhibitor as an active ingredient. The administration form of the preventive or therapeutic agent for age-related macular degeneration of the present invention includes eye drops, injections, oral agents (tablets, granules, dispersions, capsules), ointments, and creams. The form of these pharmaceutical compositions can be formulated by combining with a pharmaceutically acceptable carrier.

3 Claims, 1 Drawing Sheet

(56) References Cited

OTHER PUBLICATIONS

Liao, Tianjiang et al., "Blockade of the Interaction of Leukotriene B4 with Its Receptor Prevents Development of Autoimmune Uveitis," Investigative Ophthalmology & Visual Science, vol. 47, No. 4, Apr. 2006, pp. 1543-1549.
Talahalli, Ramaprasad et al., "Increased Synthesis of Leukotrienes in the Mouse Model of Diabetic Retinopathy," Investigative Ophthalmology & Visual Science, vol. 51, No. 3, Mar. 2010, pp. 1699-1708.
Tager, Andrew M. et al., "BLT1 and BLT2: the leukotriene $B_4$ receptors," Prostaglandins, Leukotrienes and Essential Fatty Acids, vol. 69, 2003, pp. 123-134.
Ambati, Jayakrishna et al., "Immunology of age-related macular degeneration," Nature Reviews Immunology, vol. 13, Jun. 2013, pp. 438-451.
Syed, Basharut A. et al., "Wet AMD market," Nature Reviews Drug Discovery, vol. 11, Nov. 2012, pp. 827-828.

\* cited by examiner

PREVENTIVE OR THERAPEUTIC AGENT FOR AGE-RELATED MACULAR DEGENERATION

TECHNICAL FIELD

The present invention relates to a preventive or therapeutic agent for age-related macular degeneration.

BACKGROUND ART

Age-related macular degeneration (AMD) is a progressive chronic eye disease associated with aging. Damage occurs in the macula at the center of the retina, and the quality of life (QOL) of a patient is significantly reduced as a result of degradation due to a reduction in the field of vision and distortion. The retina is made up of retinal ganglion cells, visual cells that receive light, and retinal pigment epithelia (RPE) as a lower layer for these cells. Furthermore, the outside of the retina is covered with the Bruch membrane, the choroid, and the sclera. AMD is classified as exudative (wet) AMD caused by abnormal angiogenesis from the choroid extending to immediately below the retina and leakage of the blood vessel contents, and atrophic (dry) AMD caused by direct damage to the nerve cells and RPE layer structure, without angiogenesis, and AMD in Japanese patients is most often the exudative type.

According to past research, AMD is believed to be induced by the following mechanism. First, endogenous ligands such as complementary component (C1q), amyloid β, and the like accumulate with aging, and inflammatory signals are activated through inflammasomes and TLR (Toll-like receptors) when the RPE is subjected to excessive stimulation from the endogenous ligands. Furthermore, the RPE undergoes apoptosis when subjected to oxidative stress in conjunction with aging, and therefore the barrier between the retina and the blood vessels is weakened. Next, macrophages, dendritic cells and immune cells such as NKT cells derived from peripheral blood invade to the lower layer of the retina. Furthermore, in an inflammatory environment, these cell populations promote angiogenesis by releasing inflammatory cytokines (IL-1β, TNF, IL-6) and vascular endothelial growth factor (VEGF) (Non-patent document 1).

The method for treating AMD uses anti-VEGF drugs that target VEGF, such as Ranibizumab, Bevacizumab, Pegaptanib, Aflibercept, and the like (Non-patent document 2).

CITATION LIST

Non-Patent Documents

Non-patent document 1: Ambati, J. et al., Nature Rev. Immunol. 2013, 13, 438-451
Non-patent document 2: Syed, B. A. et al., Nature Rev. Drug Discov. 2012, 11, 827

SUMMARY OF THE INVENTION

Problems to be Solved by the Invention

However, conventional AMD therapeutic agents have problems such as (1) a need to repeatedly administer the drug into the eye, and the associated risk (infection and the like); (2) the burden of high treatment cost; and (3) side effects (increased intraocular pressure, vision loss, eye pain, and retinal hemorrhaging), and the like.

Therefore, an object of the present invention is to provide a new preventive or therapeutic agent for AMD that is distinct from VEGF targeting drug.

Means for Solving Problems

Therefore, the present inventors studied the relationship between AMD and the signals of leukotriene $B_4$ ($LTB_4$) and $LTB_4$ receptor 1 (BLT1, gene name: LTB4R (human), Ltb4r1 (mouse)) using BLT1 deficient mice. As a result, they found that progressive angiogenesis related to aging was suppressed in BLT1 deficient mice compared to wild type mice, and that angiogenesis could be suppressed by intraocular administration of a BLT1 antagonist or $LTB_4$ biosynthesis inhibitors, and thus the present invention was achieved.

In other words, the present invention provides a preventive or therapeutic agent for an age-related macular degeneration (AMD), comprising a BLT1 antagonist or a $LTB_4$ biosynthesis inhibitor as an active ingredient.

The present invention also provides a BLT1 antagonist or a $LTB_4$ biosynthesis inhibitor for use in preventing or treating AMD.

The present invention also provides use of a BLT1 antagonist or a $LTB_4$ biosynthesis inhibitor for the production of a preventive or therapeutic agent for AMD.

The present invention also provides a method for preventing or treating AMD, comprising administering an effective amount of a BLT1 antagonist or a $LTB_4$ biosynthesis inhibitor.

Effects of the Invention

The preventive or therapeutic agent for AMD according to the present invention has a completely different mechanism of action than a conventional AMD therapeutic agent, and is not an antibody drug, so the cost is not expensive.

DESCRIPTION OF THE PREFERRED EMBODIMENTS

Figure 1:
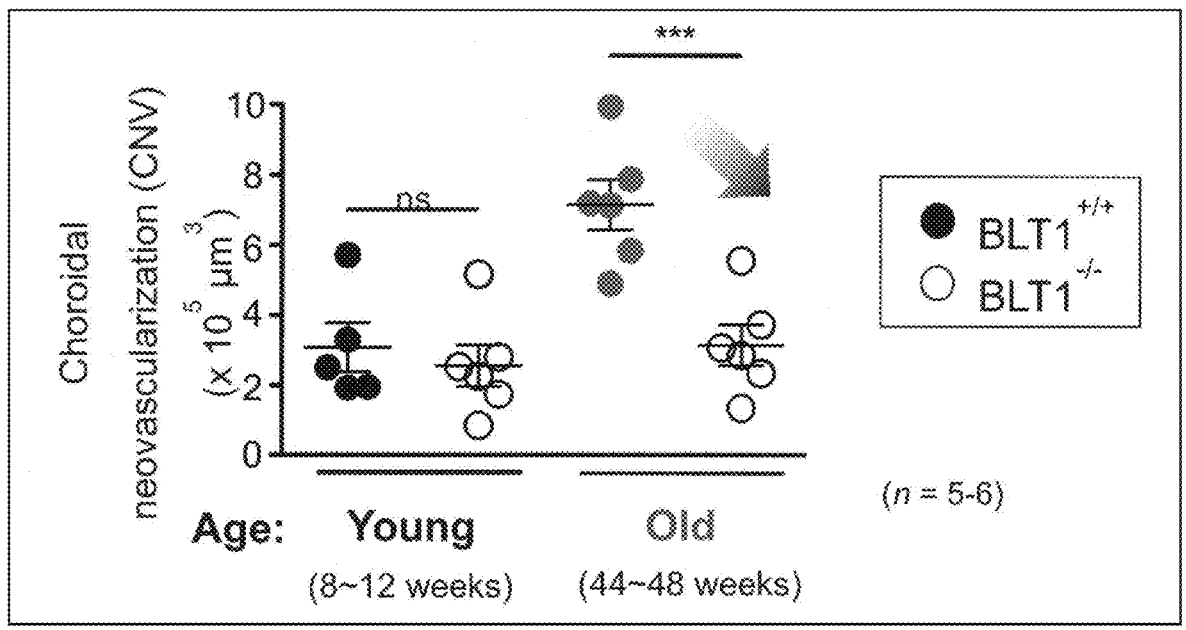
FIG. 1 The volume of choroidal neovascularization (CNV) generated from the choroid plexus to the retinal lower layer was measured after laser irradiation of the eyes of young and old BLT1 wild ($BLT1^{+/+}$) and BLT1 deficient ($BLT1^{-/-}$) mice. The figure shows that CNV that increases with age was suppressed by a deficiency of BLT1.
Figure 2:
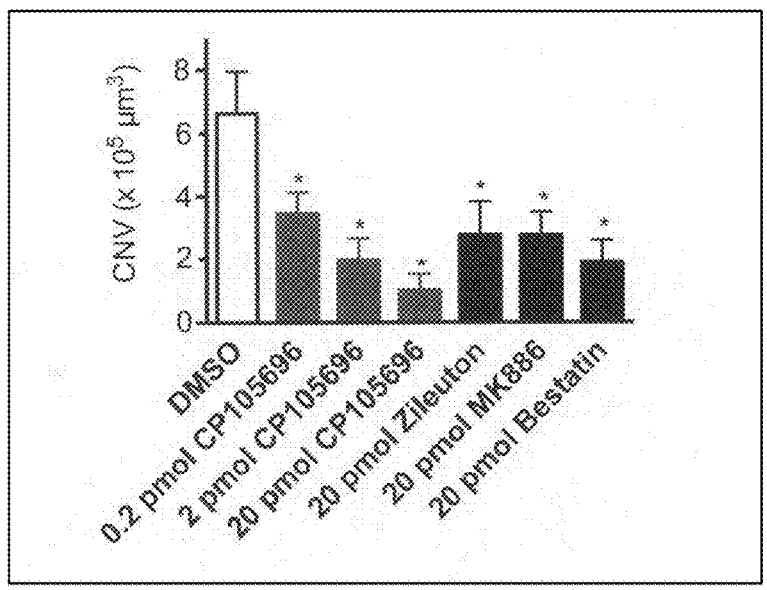
FIG. 2 The figure shows the suppressive effect of a BLT1 antagonist (CP105696) and $LTB_4$ biosynthesis inhibitors (zileuton, bestatin, and MK886) on AMD onset.

The active ingredient of the preventive or therapeutic agent for AMD of the present invention is a BLT1 antagonist or a $LTB_4$ biosynthesis inhibitor.

The first receptor of $LTB_4$ is BLT1, and this is a receptor identified by the present inventors (Yokomizo, Nature, 1997, 387, 620-624). The present inventors also studied the pathophysiological role of BLT1, and discovered that the pathological condition of a BLT1 deficient mouse was milder than a wild mouse in models of contact dermatitis, bronchial asthma, multiple sclerosis, and the like (Toda, Biochemie, 2010, 92, 682-691, Terawaki, J. Immunol. 2005, 175, 4217-4225, Kihara, BBRC, 2010, 394, 673-624).

However, there are no reports concerning the relationship between BLT1 and eye diseases.

The BLT1 antagonist is not particularly restricted, so long as binding of LTB$_4$ to BLT1 is hindered, and examples include the compounds of the following groups (1) through (6).

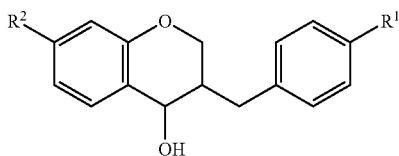

(1)

(in the formula, R$^1$ represents a hydrogen atom or a phenyl group, R$^2$ represents a 2-carboxy-4-trifluoromethyl-phenyl group or a 1-carboxy-cyclopentyl group)

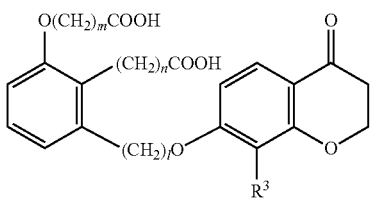

(2)

(in the formula, l, m, and n each represent an integer of from 2 to 6, and R$^3$ represents a C$_1$ to C$_4$ alkyl group)

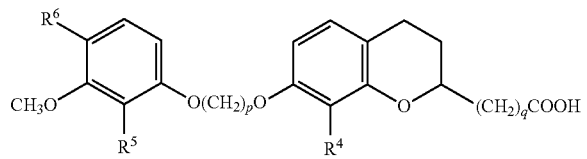

(3)

(in the formula, p represents an integer of from 2 to 6, q represents an integer of from 0 to 3, R$^4$ and R$^5$ each represent a C$_1$ to C$_4$ alkyl group or a cyclopropylmethyl group, and R$^6$ represents an acetyl group, N-methylcarbamoyl group, or a thiazolyl group)

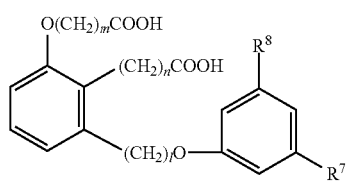

(4)

(in the formula, R$^7$ represents a 2H-1,3-benzodioxol-5-yl group, R$^8$ represents a 2-thienyl group, and l, m, and n each represent an integer of from 2 to 6)

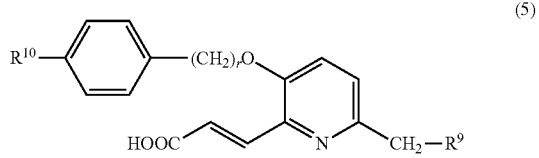

(5)

(in the formula, r represents an integer of from 2 to 8, R$^9$ represents a 3-carboxy-benzylthio group, 3-amino-phenyl sulfinyl group, or a 2,6-dichlorophenylthio group, and R$^{10}$ represents a hydrogen atom or a methoxy group)

(6)
4-[(3-[4-[2-(4-hydroxyphenyl)propan-2-yl]phenoxymethyl]phenyl)methoxy]benzene-2-carboximidamide (BIIL260),
4-[(3-[4-[2-(4-hydroxyphenyl)propan-2-yl]phenoxymethyl]phenyl)methoxy]benzene-2-N-ethoxycarbonyl-carboximidamide (amelubant), moxilubant maleate,
7-(4-(1-hydroxy-3Z-nonenyl)phenyl)-5S-hydroxy-6Z-heptenoic acid lithium salt (SL 45694),
(5S)-6-[6-[(1E,3R,5Z)-3-hydroxyundeca-1,5-dienyl]pyridin-2-yl]hexane-1,5-diol (U 75302),
5-[2-(2-carboxyethyl)-3-[(E)-6-(4-methoxyphenyl)hex-5-enoxy]phenoxy]pentanoic acid (ONO-4057),
(E)-7-carboxy-3-((6-(4-methoxyphenyl)-5-hexenyl)oxy)-9-oxo-9H-xanthene-4-propanoic acid (LY 210073),
2-[3-[3-[2-ethyl-4-(fluorophenyl)-5-hydroxyphenoxy]propoxy]-2-propylphenoxy]benzoic acid (etalocib),
1-(5-ethyl-2-hydroxy-4-[[6-methyl-6-(1H-tetrazol-5-yl)-heptyl]oxy]-phenyl]ethanone (LY 255283),
3-[[3-(2-carboxyethyl)-4-[[(5E)-6-(4-methoxyphenyl)hex-5-en-1-yl]oxy]phenyl]carbonyl]benzoic acid (LY 223982), 4,6-diphenyl-2-(3-(1H)tetrazolyl)pentyloxypyridine (CHEMBL 95799), and 2,2-dimethyl-7-[3-(3-phenylpropyl)thiophen-2-yl]heptanoic acid (RP 66153). Specific examples of the BLT1 antagonist include
1-[(3S,4R)-4-hydroxy-3-[(4-phenyl phenyl)methyl]chroman-7-yl]cyclopentane-1-carboxylic acid (CP 105696),
2-[(3S,4R)-4-hydroxy-3-(phenylmethyl)chroman-7-yl]-4-(trifluoromethyl)benzoic acid (CP 195543),
6-[2-(2-carboxyethyl)-3-[6-[(4-oxo-8-propyl-2,3-dihydrochromen-7-yl)oxy]hexyl]phenoxy]hexanoic acid (CHEMBL 86900),
5-[2-(2-carboxyethyl)-3-[6-[(4-oxo-8-propyl-2,3-dihydrochromen-7-yl)oxy]hexyl]phenoxy]pentanoic acid (CHEMBL 95453),
3-[(2 S)-7-[3-(2-cyclopropylmethyl)-3-methoxy-4-(methylcarbamoyl)phen oxy]propoxy]-8-propyl-3,4-dihydro-2H-chromen-2-yl]propanoic acid (CHEMBL 419948),
3-(7-[3-[2-cyclopropylmethyl]-3-methoxy-4-(methylcarbamoyl)phenoxy]propoxy]-8-propyl-3,4-dihydro-2H-chromen-2-yl)propanoic acid (CHEMBL 328492),
7-[3-[2-(cyclopropylmethyl)-3-methoxy-4-(1,3-thiazol-4-yl)phenoxy]propoxy]-8-propyl-3,4-dihydro-2H-chromen-2-carboxylic acid (SC 50605),
7-[3-(4-acetyl-3-methoxy-2-propylphenoxy)propoxy]-8-propylchroman-2-carboxylic acid (SC-41930),
4-(3-[6-[3-(2H-1,3-benzodioxol-5-yl)-5-(thiophen-3-yl)phenoxy]hexyl]-2-(2-carboxyethyl)phenoxy)butanoic acid (RO 5101576), ticolubant,
(E)-3-(((((6-(2-carboxyethenyl)-5-((8-(4-methoxyphenyl)octyl)oxy)-2-pyridinyl)methyl)thio)methyl)benzoic acid (CHEMBL 422598),
(E)-3-[6-[(3-aminophenyl)sulfinylmethyl]-3-[8-(4-methoxyphenyl)octoxy]pyridin-2-yl]prop-2-enoic acid (SB 201146), 4-[(3-[4-[2-(4-hydroxyphenyl)propan-2-yl]phenoxymethyl]phenyl)methoxy]benzene-2-carboximidamide (BIIL260),
4-[(3-[4-[2-(4-hydroxyphenyl)propan-2-yl]phenoxymethyl]phenyl)methoxy]benzene-2-N-ethoxycarbonyl-carboximidamide (amelubant), moxilubant maleate,
7-(4-(1-hydroxy-3Z-nonenyl)phenyl)-5S-hydroxy-6Z-heptenoic acid lithium salt (SL 45694),
(5 S)-6-[6-[(1E,3,R5Z)-3-hydroxyundeca-1,5-dienyl]pyridin-2-yl]hexane-1,5-diol (U 75302),
5-[2-(2-carboxyethyl)-3-[(E)-6-(4-methoxyphenyl)hex-5-enoxy]phenoxy]pentanoic acid (ONO-4057),
(E)-7-carboxy-3-((6-(4-methoxyphenyl)-5-hexenyl)oxy)-9-oxo-9H-xanthene-4-propanoic acid (LY 210073),
2-[3-[3-[2-ethyl-4-(fluorophenyl)-5-hydroxyphenoxy]propoxy]-2-propylphenoxy]benzoic acid (etalocib),
1-(5-ethyl-2-hydroxy-4-[[6-methyl-6-(1H-tetrazol-5-yl)-heptyl]oxy]-phenyl]ethanone (LY 255283),
3-[[3-(2-carboxyethyl)-4-[[(5E)-6-(4-methoxyphenyl)hex-5-en-1-yl]oxy]phenyl]carbonyl]benzoic acid (LY 223982), 4,6-diphenyl-2-(3-(1H)tetrazolyl)pentyloxypyridine (CHEMBL 95799), and 2,2-dimethyl-7-[3-(3-phenylpropyl)thiophen-2-yl]heptanoic acid (RP 66153).

These compounds exemplified as BLT1 antagonists are all known compounds and can be produced, for example, by the method disclosed in JP-A-H7-502536, EP 0743064 A1, WO 95/33742, JP-A-H11-503737, JP-A-H5-25159, and the like. More specifically, the compounds of formula (1) are disclosed in JP-A-H7-502536, U.S. Pat. No. 5,552,435, and the like, the compounds of formulas (2) and (3) are disclosed in EP 0743064 A1, and the like, the compounds of (6) are disclosed in JP-A-H11-503737, and the like, and the compounds of the other formulas are disclosed in JP-A-H5-25159, WO 95/33742, and the like. In addition, these compounds are found in IUPHAR DATABASE and Pubchem OPEN CHEMISTRY DATABASE.

These BLT1 antagonists and $LTB_4$ biosynthesis inhibitors significantly suppress angiogenesis of the choroid of the AMD model, and are useful as preventive or therapeutic agents for AMD.

Any of the $LTB_4$ biosynthesis inhibitors may be used, so long as it inhibits the biosynthesis of $LTB_4$, and for example, inhibitors for a $LTB_4$ producing enzyme may be mentioned. Examples of the $LTB_4$ biosynthesis inhibitor include zileuton (N-[1-(1-benzothien-2-yl)ethyl]-N-hydroxyurea), bestatin (N-[(2S,3R)-3-amino-2-hydroxy-4-phenylbutyryl]-L-leucine), MK-886 (1-[(4-chlorobenzyl)methyl]-3-[(1,1-dimethylethypthio]-α,α-dimethyl-5-(1-methylethyl)-1H-indole-2-propanoic acid), caffeic acid, licofelone, 3,4-dihydroxyphenyl ethanol, CAY10649 ((Z)-2-(4-chlorophenyl)-5-(4-methoxybenzylidene)thiazol-4(5H)-one), and captopril.

Examples of the administration form of the preventive or therapeutic agent for AMD of the present invention include eye drops, injections, oral agent (tablets, granules, dispersions, capsules), ointments, and creams. Of these, eye drops are particularly preferable. The form of these pharmaceutical compositions can be formulated by combining with a pharmaceutically acceptable carrier. Examples of the carrier include lactose, glucose, D-mannitol, starch, crystalline cellulose, calcium carbonate, kaolin, starch, gelatin, hydroxypropyl cellulose, hydroxypropyl methyl cellulose, polyvinylpyrrolidone, ethanol, carboxymethyl cellulose, calcium carboxymethyl cellulose, magnesium stearate, talc, acetyl cellulose, sucrose, titanium oxide, benzoic acid, p-hydroxybenzoic acid esters, sodium dehydroacetate, gum arabic, tragacanth, methylcellulose, egg yolk, surfactants, sucrose, simple syrups, citric acid, distilled water, ethanol, glycerin, propylene glycol, macrogol, disodium hydrogen phosphate, sodium dihydrogen phosphate, sodium phosphate, glucose, sodium chloride, phenol, thimerosal, p-hydroxybenzoic acid esters, and sodium bisulfite, and these can be used by blending with the BLT1 antagonists depending on the form of the preparation.

Furthermore, the amount of BLT1 antagonist or $LTB_4$ biosynthesis inhibitor included in the pharmaceutical composition preparation of the present invention varies dramatically depending on the form of the preparation, and although not restricted in particular, the amount is normally 0.01 to 100 weight %, preferably 1 to 100 weight %, based on the total amount of the composition.

The dosage of the preventive or therapeutic agent for AMD of the present invention varies depending on the symptoms and age of the patient receiving the administration, and the administration method, but the dosage is preferably 0.01 to 100 mg/kg/day as a BLT1 antagonist or $LTB_4$ biosynthesis inhibitor.

EXAMPLES

The present invention is described below in further detail by presenting examples.

Test Example 1

Angiogenesis that occurred from the choroid plexus after laser injury was analyzed using C57BL/6 background BLT1 wild type ($BLT1^{+/+}$) mice and BLT1 deficient ($BLT1^{-/-}$) mice.

Laser light (power: 200 mW, exposure time: 0.10 seconds, wavelength: 532 nm) was irradiated in 4 to 5 spots onto male young (8 to 12 weeks) and old (44 to 48 weeks) $BLT1^{+/+}$ mice and $BLT1^{-/-}$ mice, and after 7 days, the eyes were isolated and fixed using a phosphate buffered saline (PBS) containing 4% paraformaldehyde (PFA), the cornea, lens, and retina were removed, and then fixed again using 4% PFA/PBS. The ocular tissue containing the retinal pigment epithelia and choroid plexus were immersed in PBS containing methanol in order of 50%, 75%, 100%, 75%, 50%, and 25% to remove water, and then incubated at 4° C. for 1 hour in a blocking solution (1% bovine blood serum albumin, phosphate buffered saline containing 0.1% Triton X-100), and then stained overnight at 4° C. using isolectin B4 (IB4, 7 mg/mL) labeled with FITC. Incisions were made in the samples and the samples were molded on a slide glass, sealed with a mounting agent containing an antifading reagent, and then a cover glass was placed thereon to produce a flat mount. A three-dimensional IB4 positive blood vessels image was captured using a confocal microscope, and the volume of angiogenesis that occurred in each mouse was measured.

As shown in FIG. 1, the results indicate that there was no observable difference in the angiogenesis between $BLT1^{-/-}$ mice and $BLT1^{-/-}$ mice in the young mice group. However, angiogenesis was significantly lower in the $BLT1^{-/-}$ mice as compared to the $BLT^{+/+}$ mice in the old mice group.

From these results, it can be seen that age-related progressive angiogenesis of the retina was milder in the $BLT1^{-/-}$ mice.

Test Example 2

Immediately after laser light irradiation of C57BL/6 background old mice purchased (Japan SLC, wild mice, 40 weeks or older, male), DMSO (final: 0.1%, diluted with PBS), CP105696 (where in the formula (1), $R^1$=phenyl and $R^2$=1-carboxycyclopentyl group) which is a BLT1 antagonist, or zileuton, bestatin, or MK886 each of which is an inhibitor for $LTB_4$ production-related enzyme was administered into a vitreous body of each mouse. Similar to Test Example 1, angiogenesis from the choroid plexus was evaluated 7 days after laser irradiation.

The results showed that, in the mice administered with CP 105696, the angiogenesis volume was significantly reduced in a concentration-dependent manner. Similarly, it was observed that the inhibitors for $LTB_4$ production-related enzyme showed an effect of suppressing angiogenesis. These suggest that a BLT1 antagonist and a $LTB_4$ biosynthesis inhibitor are new therapeutic agents that suppress the onset of AMD.

The invention claimed is:

1. A method for treating age-related macular degeneration, the method comprising
    administering to a subject in need thereof an effective amount of a compound as the sole active ingredient, wherein the compound is
    1-[(3S,4R)-4-hydroxy-3-[(4-phenylphenyl)methyl]chroman-7-yl]cyclopentane-1-carboxylic acid (CP 105696).

2. The method of claim 1, wherein the compound is in a composition suitable for administration to an eye of the subject.

3. The method of claim 2, wherein the administrating comprises administering the composition directly to an eye of the subject.

* * * * *